United States Patent
Loos et al.

[19]

[11] Patent Number: 5,827,234
[45] Date of Patent: *Oct. 27, 1998

[54] DEVICE FOR ADMINISTERING IMPLANTS

[75] Inventors: Hans-Joachim Loos, Ginsheim-Gustavsburg; Günter Ziegert, Frankfurt am Main; Horst Pajunk; Heinrich Pajunk, both of Geisingen, all of Germany

[73] Assignee: Hoechst Aktiengesellschaft, Frankfurt am Main, Germany

[ * ] Notice: The term of this patent shall not extend beyond the expiration date of Pat. No. 5,520,660.

[21] Appl. No.: 565,837

[22] Filed: Dec. 1, 1995

Related U.S. Application Data

[63] Continuation of Ser. No. 262,899, Jun. 21, 1994, Pat. No. 5,520,660.

[30] Foreign Application Priority Data

Jun. 23, 1993 [DE] Germany .......................... 43 20 754.5

[51] Int. Cl.⁶ .................................................. A61M 5/315
[52] U.S. Cl. ........................................ 604/236; 604/234
[58] Field of Search ..................... 604/236, 240, 604/247–249, 33, 59–61, 181, 906, 156, 152, 124, 125, 221, 226, 234; 600/34, 35; 251/149.6, 149.7; 137/329.1–329.3, 901; 128/749, 762, 754, 748; 623/11

[56] References Cited

U.S. PATENT DOCUMENTS

| 2,490,553 | 12/1949 | Smith .......................................... 604/89 |
|---|---|---|
| 3,550,861 | 12/1970 | Teson ....................................... 251/6 X |
| 3,757,981 | 9/1973 | Harris, Sr. et al. . |
| 3,957,052 | 5/1976 | Topham . |
| 4,675,003 | 6/1987 | Hooven . |
| 4,729,401 | 3/1988 | Raines . |
| 4,787,384 | 11/1988 | Campbell et al. . |
| 4,838,866 | 6/1989 | Marshall, Sr. ........................... 604/152 |
| 5,261,895 | 11/1993 | Kablik . |
| 5,356,394 | 10/1994 | Farley et al. . |
| 5,489,274 | 2/1996 | Chu et al. ................................. 604/167 |
| 5,514,114 | 5/1996 | Soto-Tolosa et al. ................... 604/275 |

FOREIGN PATENT DOCUMENTS

| 245802 | 2/1960 | Australia . |
|---|---|---|
| 304700 | 3/1989 | European Pat. Off. . |
| 3802158 A1 | 2/1989 | Germany . |
| 786850 | 11/1957 | United Kingdom . |
| WO 92/15362 | 9/1992 | WIPO . |

OTHER PUBLICATIONS

European Search Report for European Appln. No. 94109161.3 dated Oct. 31, 1994.

*Primary Examiner*—Wynn Wood Coggins
*Assistant Examiner*—A. T. Nguyen
*Attorney, Agent, or Firm*—Finnegan, Henderson, Farabow, Garrett & Dunner, L.L.P.

[57] ABSTRACT

In the device for administering implants, which comprises an active substance container with injection cannula and plunger, the plunger is arranged in a plunger channel. The plunger channel merges with continuity into the lumen of the cannula. A holder device (5) for the implant (2) is arranged at the lumen-side end of the plunger channel (3).

8 Claims, 2 Drawing Sheets

DEVICE FOR ADMINISTERING IMPLANTS

This is a continuation of application Ser. No. 08/262,899, filed Jun. 21, 1994 now U.S. Pat. No. 5,520,660.

BACKGROUND OF THE INVENTION

1. Field of the Invention

The invention relates to a device for administering implants, comprising an active substance container with injection cannula and plunger, the plunger being arranged in a plunger channel which merges with continuity into the lumen of the cannula.

2. Discussion of the Related Art

Devices of the type mentioned are known from DE 3 802 158 A1. A disadvantage of these devices is that the rod-shaped implant, which can contain a medicament, can slip out of the plunger channel, which at the same time forms the implant chamber, and slip through the lumen of the cannula, as a result of which the implant cannot be used for administration.

3. Summary of the Invention

The invention is intended to rectify this. The object is achieved by means of the device which is mentioned at the start, and in which a holder device for the implant is arranged in the plunger channel.

The holder device can comprise two elastic pins which are arranged opposite one another and which in each case have a rounded end protruding into the plunger channel. The holder device can moreover comprise two spring-loaded pins which are arranged opposite one another and which in each case have a rounded end protruding into the plunger channel. In a further embodiment, the holder device can comprise at least one spring-loaded ball, preferably two spring-loaded balls, protruding into the plunger channel.

The holder device not only prevents the inadvertent escape of the implant from the administration device, but also frees the plunger channel without damaging the implant.

The invention is explained in greater detail hereinbelow with reference to drawings which show only one embodiment.

BRIEF DESCRIPTION OF THE DRAWINGS

FIG. 4 shows, in a sectional view, an alternative embodiment of the holder with only one retaining element.

DESCRIPTION OF THE PREFERRED EMBODIMENTS

Figure 1:
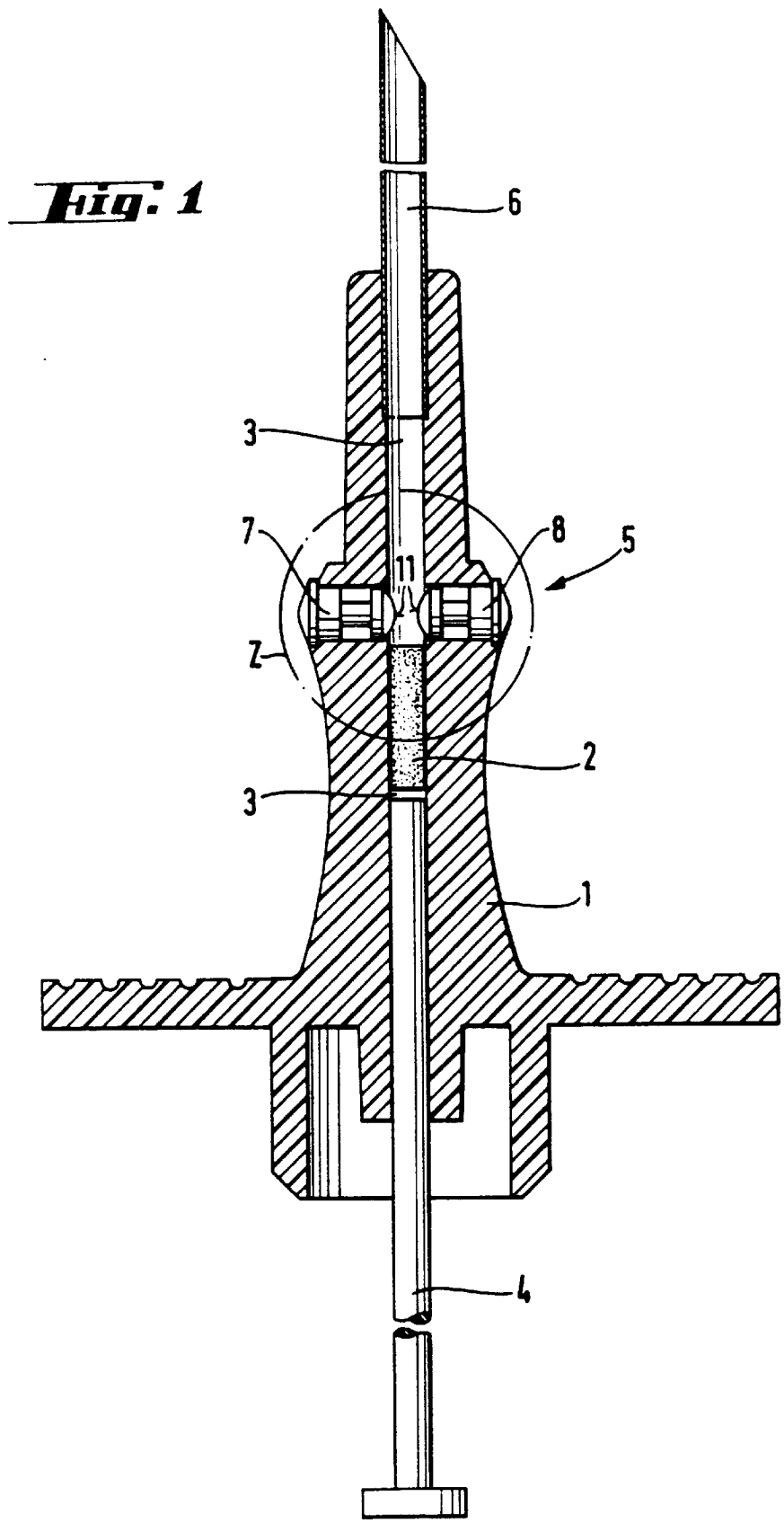
FIG. 1 shows, in a sectional view, the device for administering implants.
Figure 2:
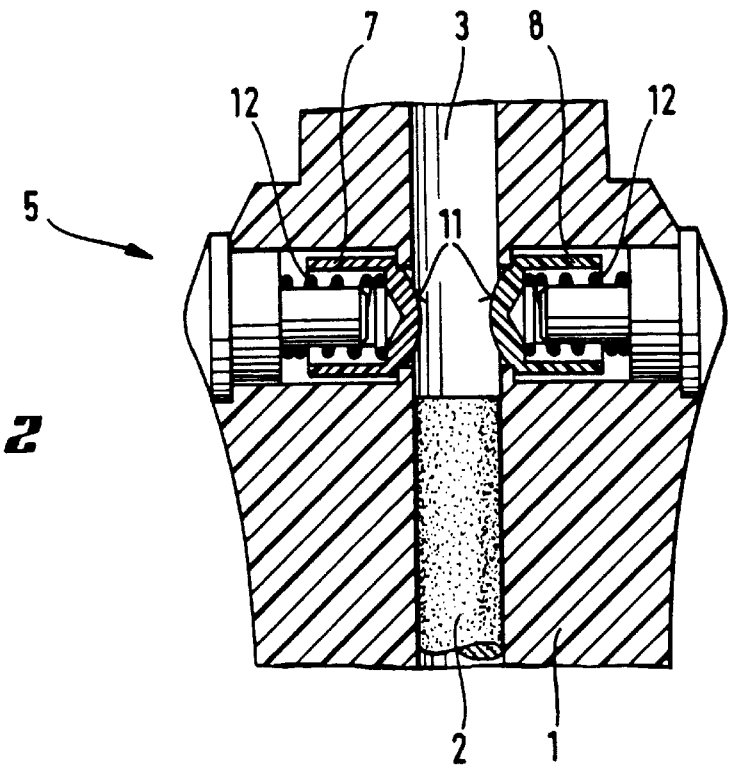
FIG. 2 shows, in a sectional view, the detail "Z" in an alternative embodiment of the holder device.
Figure 3:
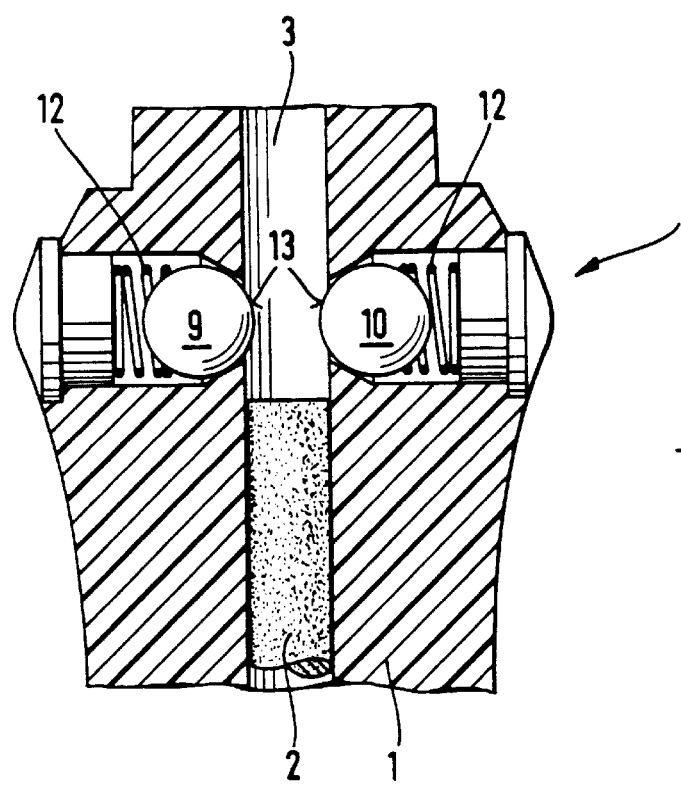
FIG. 3 shows, in a sectional view, the detail "Z" in a further alternative embodiment of the holder device.

The device for administering implants, so-called rods, comprises an active Substance container 1 with injection cannula 6 and plunger 4. The plunger 4 is arranged in a plunger channel 3, which also receives the preferably rod-shaped implant 2 and thus serves as an implant chamber. The plunger channel 3 must merge with continuity into the internal channel or lumen of the cannula 6 so that cross-sectional variations are avoided on the route which the implant takes on being administered. In order to ensure that the implant 2 cannot leave the active substance container 1 inadvertently, a holder device 5 for the implant 2 is provided at the lumen-side end of the plunger channel 3. The holder device 5 protrudes slightly into the plunger channel 3 and thus forms an obstacle for the implant 2. In order to avoid deformations of the implant and/or abrasion of the implant during administration, the holder device 5 should be designed or arranged such that it moves out of the way of the implant, without damaging the latter, and so clears the way. The holder device 5 can comprise at least one pin, normally two pins 7, 8, in each case having a rounded end 11. The pins 7, 8 can be made of elastic material from various rubber types or the like (FIG. 1). Similarly, pins 7, 8 made of non-elastic material, which are held in position by the pressure of springs 12, are suitable (FIG. 2). In the case of the rigid bolts 7, 8 too, the end 11 protruding into the plunger channel 3 can be rounded. Instead of the pins 7, 8, balls which protrude into the plunger channel 3 via their spherical caps 13 are equally suitable (FIG. 3). The balls 9, 10 can, like the pins 7, 8, be made of elastic material or be held in their position with a spring 12. Spring resilience, elasticity and surface rounding should be such that the implant can pass the holder device 5 without deformation and/or abrasion losses.

What is claimed is:

1. A device for administering implants, comprising:
   an active substance container including an injection cannula having an internal channel, a plunger channel coaxial with the internal channel of the cannula, and a plunder movable within the plunger channel; and
   a retaining element including a spring-loaded ball biased to at least partially protrude into the plunger channel and displaceable in a direction perpendicular to a longitudinal axis of the plunger channel, for engaging and preventing inadvertent movement of an implant through the plunger channel.

2. The device of claim 1, wherein the retaining element is configured to prevent deformation and abrasion of the implant as the plunger moves the implant through the plunger channel.

3. The device of claim 1, wherein the retaining element is recessible in an opening in a side wall of the container to allow movement of the implant through the plunger channel.

4. The device of claim 1, wherein the retaining element is displaceable between a first position partially protruding into the plunger channel and a second position outside the plunger channel, the retaining element engaging and preventing inadvertent movement of an implant through the channel in the first position, and clearing the plunger channel to permit passage of an implant through the plunger channel in the second position.

5. A device for administering implants, comprising:
   an active substance container including an injection cannula having an internal channel, a plunger channel coaxial with the internal channel of the cannula, and a plunger movable within the plunger channel; and
   a pair of opposed spring-loaded balls for engaging and preventing inadvertent movement of an implant through the plunger channel, each ball biased to protrude into the plunger channel.

6. The device of claim 5, wherein the spring-loaded balls are configured to prevent deformation and abrasion of the implant as the plunger moves the implant through the plunger channel.

7. The device of claim 5, wherein the spring-loaded balls are recessible in an opening in a side wall of the container to allow movement of the implant through the plunger channel.

8. The device of claim 5, wherein the retaining elements are displaceable between a first position partially protruding into the plunger channel and a second position outside the plunger channel, the retaining elements engaging and preventing inadvertent movement of an implant through the channel in the first position, and clearing the plunger channel to permit passage of an implant through the plunger channel in the second position.

* * * * *

UNITED STATES PATENT AND TRADEMARK OFFICE
CERTIFICATE OF CORRECTION

PATENT NO. : 5,827,234
DATED : October 27, 1998
INVENTOR(S) : LOOS et al.

It is certified that error appears in the above-identified patent and that said Letters Patent is hereby corrected as shown below:

Claim 1, column 2, line 29, "plunder" should read --plunger--.

Signed and Sealed this

Eighth Day of June, 1999

Attest:

Q. TODD DICKINSON

*Attesting Officer*           *Acting Commissioner of Patents and Trademarks*